United States Patent
Avni

(10) Patent No.: US 10,646,668 B2
(45) Date of Patent: May 12, 2020

(54) PULSATING INHALER AND A METHOD OF TREATING UPPER RESPIRATORY DISORDERS

(71) Applicant: Respinova Ltd., Herzliya Pituach (IL)

(72) Inventor: Yuval Avni, Tel Aviv (IL)

(73) Assignee: RESPINOVA LTD., Herzliya Pituach (IL)

( * ) Notice: Subject to any disclaimer, the term of this patent is extended or adjusted under 35 U.S.C. 154(b) by 0 days.

(21) Appl. No.: 14/522,694

(22) Filed: Oct. 24, 2014

(65) Prior Publication Data

US 2015/0040891 A1 Feb. 12, 2015

Related U.S. Application Data

(63) Continuation-in-part of application No. 11/916,306, filed as application No. PCT/IL2006/000611 on May 24, 2006, now abandoned.

(30) Foreign Application Priority Data

Jun. 2, 2005 (IL) .......................... 168975

(51) Int. Cl.
*A61M 15/00* (2006.01)
*A61M 11/00* (2006.01)
(Continued)

(52) U.S. Cl.
CPC ........ *A61M 15/003* (2014.02); *A61M 11/005* (2013.01); *A61M 11/007* (2014.02);
(Continued)

(58) Field of Classification Search
CPC .............. A61M 15/003; A61M 11/042; A61M 11/007; A61M 11/005; A61M 15/009;
(Continued)

(56) References Cited

U.S. PATENT DOCUMENTS 2,261,838 A * 11/1941 Allendorff ............... G01H 1/10
73/650
2,670,739 A * 3/1954 McNeill ............ A61M 15/0025
128/200.18
(Continued)

FOREIGN PATENT DOCUMENTS

WO 2005046426 5/2005
WO WO 2006129304 A2 * 12/2006 .......... A61M 11/005

OTHER PUBLICATIONS

International Search Report dated Mar. 29, 2007 for PCT/IL06/000611.
(Continued)

*Primary Examiner* — Timothy A Stanis
*Assistant Examiner* — Victoria Murphy
(74) *Attorney, Agent, or Firm* — The Roy Gross Law Firm, LLC; Roy Gross

(57) ABSTRACT

A pulsating inhaler comprising: (a) a fluid oscillator providing focused fluid columns with a series of alternating high and low pressure zones and (b) at least one outlet orifice adapted for delivering said focused fluid column to the respiratory tract of said patient. The fluid oscillator further comprises a piston which is actuated by a motor with an eccentric mechanism. According to alternative embodiment of the invention, the fluid oscillator comprises a rotating disc having a missing section.

5 Claims, 9 Drawing Sheets

(51) Int. Cl.
*A61M 11/04* (2006.01)
*A61M 16/00* (2006.01)

(52) U.S. Cl.
CPC ........ *A61M 11/042* (2014.02); *A61M 15/009* (2013.01); *A61M 15/0035* (2014.02); *A61M 16/0006* (2014.02); *A61M 16/0066* (2013.01); *A61M 2016/0036* (2013.01); *A61M 2202/0225* (2013.01); *A61M 2202/064* (2013.01); *A61M 2202/066* (2013.01); *A61M 2205/6009* (2013.01); *A61M 2205/6036* (2013.01); *A61M 2205/6045* (2013.01); *A61M 2205/6072* (2013.01)

(58) Field of Classification Search
CPC ........ A61M 16/0006; A61M 2202/064; A61M 15/0035; A61M 2205/6036; A61M 16/0066; A61M 2202/0225; A61M 2205/6009; A61M 2205/6045; A61M 2205/6072; A61M 2202/066; A61M 2016/0036
See application file for complete search history.

(56) References Cited

U.S. PATENT DOCUMENTS

| | | | | |
|---|---|---|---|---|
| 3,120,228 A * | 2/1964 | Huxley, III | ............ | A61H 31/00 601/44 |
| 3,584,621 A * | 6/1971 | Bird | ............ | A61M 16/00 128/200.18 |
| 3,608,866 A * | 9/1971 | Karpacheva | ............ | B01F 11/0071 366/106 |
| 3,948,286 A * | 4/1976 | Dunbar | ............ | A61M 16/10 137/870 |
| 3,971,377 A * | 7/1976 | Damani | ............ | A61M 15/0028 128/200.17 |
| 4,253,468 A * | 3/1981 | Lehmbeck | ............ | A61B 5/09 128/200.18 |
| 4,770,165 A * | 9/1988 | Hayek | ............ | A61H 31/02 601/43 |
| 4,770,413 A * | 9/1988 | Green | ............ | A63B 23/18 137/269.5 |
| 4,930,498 A * | 6/1990 | Hayek | ............ | A61H 31/02 128/205.26 |
| 5,388,571 A * | 2/1995 | Roberts | ............ | A61M 16/16 128/200.18 |
| 5,388,574 A | 2/1995 | Ingebrethsen | | |
| 5,474,059 A * | 12/1995 | Cooper | ............ | A61M 11/06 128/200.22 |
| 5,613,489 A * | 3/1997 | Miller | ............ | A61M 15/0086 128/200.14 |
| 5,862,802 A * | 1/1999 | Bird | ............ | A61M 11/042 128/204.18 |
| 5,931,163 A * | 8/1999 | Stegmann | ............ | A61M 16/20 128/204.18 |
| 5,988,166 A * | 11/1999 | Hayek | ............ | A61H 31/02 128/202.12 |
| 6,066,101 A * | 5/2000 | Johnson | ............ | A61B 5/085 600/529 |
| 6,182,656 B1 * | 2/2001 | Sagiv | ............ | A61H 31/02 128/202.12 |
| 6,182,658 B1 * | 2/2001 | Hayek | ............ | F16K 11/085 128/205.24 |
| 6,192,876 B1 * | 2/2001 | Denyer | ............ | A61B 5/087 128/204.18 |
| 6,595,203 B1 * | 7/2003 | Bird | ............ | A61M 11/06 128/200.14 |
| 6,694,976 B1 * | 2/2004 | Takaki | ............ | A61M 16/0096 128/204.18 |
| 6,708,690 B1 * | 3/2004 | Hete | ............ | A61M 16/0096 128/204.18 |
| 6,708,691 B1 * | 3/2004 | Hayek | ............ | A61H 31/02 128/205.24 |
| 6,739,332 B1 * | 5/2004 | Higenbottam | ............ | A61M 11/06 128/200.13 |
| 8,251,876 B2 * | 8/2012 | Boerst | ............ | A63B 21/00196 128/203.12 |
| 8,539,951 B1 * | 9/2013 | Meyer | ............ | A61M 16/0066 128/205.24 |
| 9,114,224 B2 * | 8/2015 | Avni | ............ | A61M 16/0006 |
| 2001/0009152 A1 * | 7/2001 | Bennarsten | ............ | A61M 16/0096 128/204.21 |
| 2002/0006201 A1 | 1/2002 | Gradon et al. | | |
| 2003/0192545 A1 * | 10/2003 | Truitt | ............ | A61M 16/0006 128/204.18 |
| 2004/0025865 A1 * | 2/2004 | Nichols | ............ | A61M 11/042 128/200.14 |
| 2005/0022806 A1 | 2/2005 | Beaumont et al. | | |
| 2005/0061318 A1 * | 3/2005 | Faram | ............ | A61M 16/127 128/204.18 |
| 2008/0200848 A1 * | 8/2008 | Avni | ............ | A61H 15/0085 601/46 |
| 2009/0071470 A1 * | 3/2009 | Abrams | ............ | A61M 11/02 128/200.22 |

OTHER PUBLICATIONS

Written Opinion dated Mar. 30, 2007 for PCT/IL06/000611.
International Preliminary Report on Patentability dated Dec. 6, 2007 for PCT/IL06/000611.

* cited by examiner

PULSATING INHALER AND A METHOD OF TREATING UPPER RESPIRATORY DISORDERS

CROSS-REFERENCE TO RELATED APPLICATIONS

The present application is a continuation-in-part of U.S. patent application Ser. No. 11/916,306, filed on Dec. 3, 2011 which claims priority from IL patent application Ser. No. 168975, filed Jun. 2, 2005.

FIELD OF THE INVENTION

The present invention generally relates to a pulsating inhaler, and to a method of treating upper respiratory disorders.

BACKGROUND OF THE INVENTION

Upper respiratory disorders such as viral upper respiratory tract infections or "common cold", allergic rhinitis, and rhinosinusitis are associated with impairment in mucociliary clearance in the nasal passages. Although the causes of these disorders are varied, they share a common set of nasal symptoms such as rhinorrhea, nasal congestion/blockage, and post-nasal drip. In these conditions the mucous membranes of the nose and paranasal sinuses become irritated, leading to symptoms. In some patients, this irritation is sufficient to hinder the normal drainage of the sinuses into the nasal cavity, resulting in blockage that may lead to additional impaired ciliary activity, intense pressure/pain, and increased likelihood of infection. Allergic rhinitis (AR) is a condition that results from exposure to allergens, either at specific times of the year (seasonal allergic rhinitis) or year-round (perennial allergic rhinitis). Up to one-half of AR patients suffer from both seasonal as well as perennial AR, approximately one-third suffer from seasonal AR alone and another one-third from perennial AR alone. In either seasonal or perennial AR, the symptoms and treatment approaches are similar. Symptoms most often include nasal congestion or stuffiness, rhinorrhea and nasal itching. Allergic rhinitis affects nearly 150 million people in the world's seven major pharmaceutical markets, and annual sales of prescription products to treat allergic rhinitis are estimated to total more than $4.5 billion worldwide. The treatments currently available include primarily prescription and over-the-counter antihistamines, decongestants and nasal corticosteroids, delivered by nasal sprays, evaporation devices, and ointments.

Upper Respiratory Tract Infections (URTI) and the common cold affect all ages and are uncomfortable conditions with lost work and school days.

Asthma and COPD (chronic obstructive pulmonary disease) are chronic illnesses requiring lifetime therapy and affect 44 million Americans. The mainstay of treatment is inhaler therapies. The delivery of medications via an inhaler is problematic causing decreased efficacy and poor patient compliance. Therefore there is a constant search for improving the delivery of drugs through inhalers.

The problem with current inhalers is the tendency of deposit of the medication in the oral cavity, not in the lungs where it is effective. Also, it is difficult to coordinate the delivery of the drug with the expiratory cycle. Because of these problems the accurate dosage of medication cannot be delivered and the treatment causes many side effects. In addition the current inhaler techniques are passive techniques that are based on the ability of the patient to suck the drug to the lungs. As their action on the patient is solely and totally drug-dependent, the above-mentioned faults cause a major problem to the user.

The pulsating inhaler delivery system works on the principal of successive small pulses of air (that can contain powder or liquid) in metered doses. This enhances delivery directly to lungs and increase efficacy. It does not require positioning or coordination with breathing. Therefore, there is minimal deposition in the oral cavity and minimal associated morbidity, e.g., dry mouth, bad taste, fungal infections. By delivering the medication with pulsation of small doses there will be an increase in bioavailability thus increasing the effectiveness of current inhalation medications. This method will be suitable for all medications, therefore very attractive to the patients. There will be an increase in patient compliance due to ease of use and increased feeling of effectiveness without the side effects that are currently a problem.

The pulsating inhaler will deliver drugs using unique device specific cartridges that will be disposable.

The efficient delivery of drugs to the lungs can also serve as a treatment modality for various systemic diseases such as the delivery of inhaled insulin to treat diabetes patients. These applications require accurate dosage that is difficult to achieve with the current inhaler technology.

The device has also non-drug dependent physiologic functions as it transfers vibration to the airways. Thus causing smooth muscle relaxation, reduction of airway edema, increase in blood and lymphatic flow, improved gas exchange and oxygenation and decreased dyspnea. As the device continue to oscillate during inspiration and expiration it provides a pulsating continuous positive airway pressure (PCPAP). The PCPAP prevents the collapse of the airways of the asthma and COPD patient, during expiration, which decreases dyspnea and is highly beneficial to the patients.

BRIEF DESCRIPTION OF THE FIGURES

In order to understand the invention and to see how it may be implemented in practice, a preferred embodiment will now be described, by way of non-limiting example only, with reference to the accompanying drawing, in which.

SUMMARY OF THE INVENTION

It is hence one object of the invention to disclose a pulsating inhaler comprising: (a) a fluid oscillator providing focused fluid columns with a series of alternating high and low pressure zones and (b) at least one outlet orifice adapted for delivering said focused fluid column to the respiratory tract of said patient.

It is a core purpose of the invention to provide the fluid oscillator comprising a piston actuated by a motor with an eccentric mechanism.

Another object of the invention is to disclose the inhaler comprising a medicament dispenser dispensing fixed amounts of at least one medicament and injecting said fixed amounts of said at least one medicament into said focused fluid column.

A further object of the invention is to disclose the inhaler comprising a fluid dispenser fluidly coupled to said fluid oscillator.

A further object of the invention is to disclose the medicament dispenser activated before said fixed amounts of said at least one medicament is transported by said focused fluid column.

A further object of the invention is to disclose the medicament dispensed by puncturing a disposable capsule such that a fixed amount of said medicament is injected into said focused fluid column.

A further object of the invention is to disclose a pulsating inhaler comprising: (a) a fluid oscillator providing focused fluid columns with a series of alternating high and low pressure zones and (b) at least one outlet orifice adapted for delivering said focused fluid column to the respiratory tract of said patient, It is another core purpose of the invention to provide the fluid oscillator comprising a rotating disc having a missing section.

Figure 1:
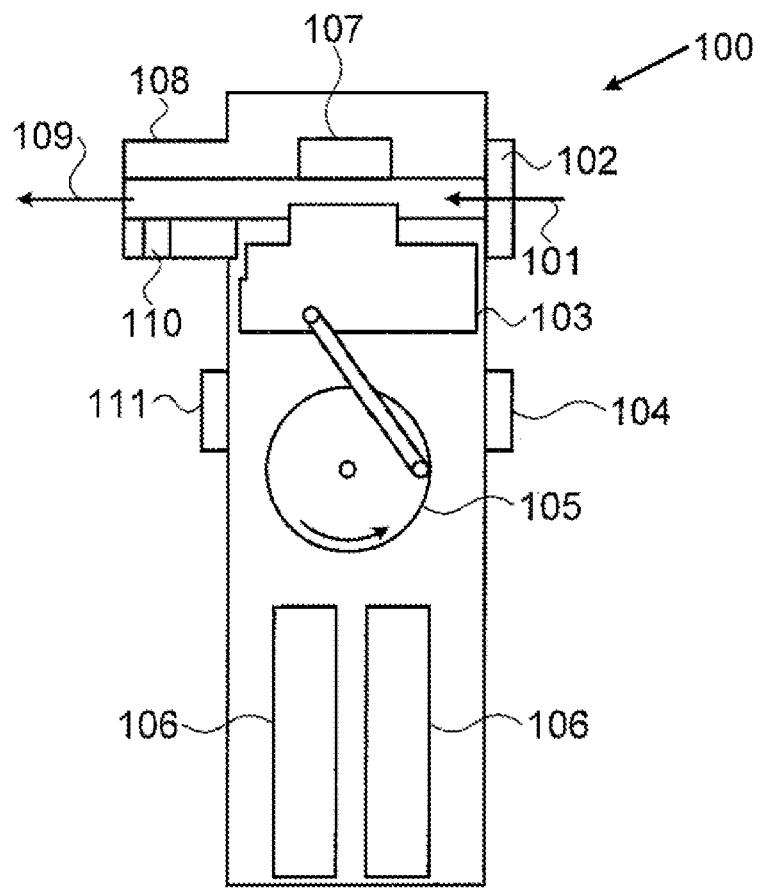
FIG. 1 schematically presents a lateral section of a piston pulsed inhaler according to an embodiment of the present invention.
Figure 2A:
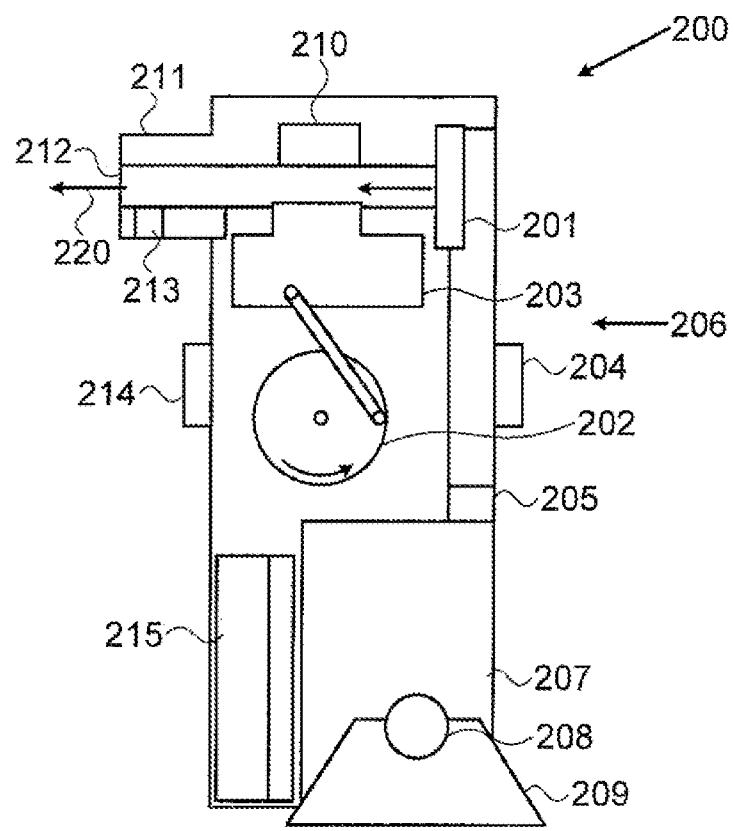
FIGS. 2A and 2B schematically presents a lateral cross section (upper view) of a piston pulsed inhaler according to another embodiment of the present invention.
Figure 2B:
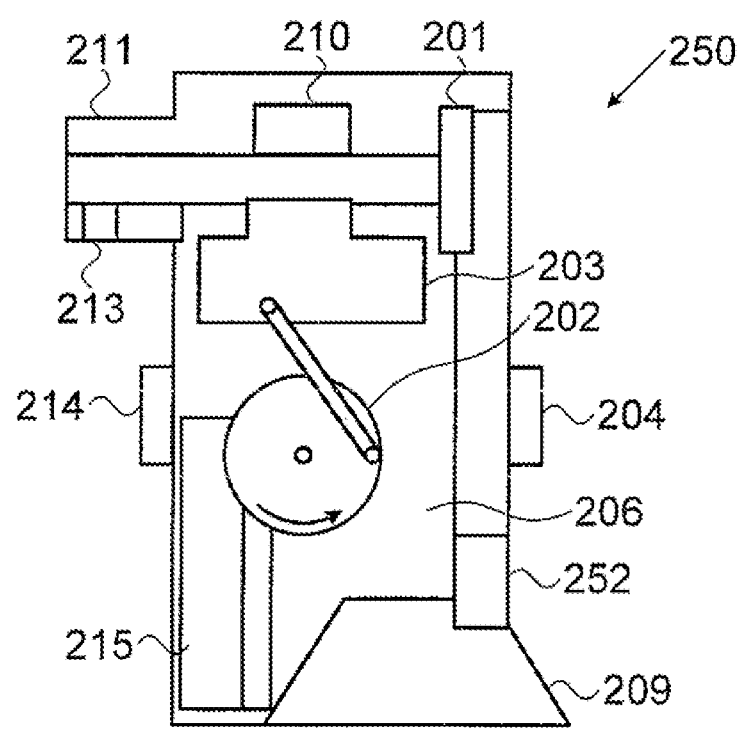

A further object of the invention is to disclose a method of administering focused fluid columns to the respiratory tract of a patient. The aforesaid method comprises the steps of: (a) providing a pulsating inhaler further comprising: (i) a fluid oscillator providing focused fluid columns with a series of alternating high and low pressure zones and (ii) at least one outlet orifice adapted for delivering said focused fluid column to the respiratory tract of said patient; (b) inhaling said focused fluid columns such that the respiratory tract of said patient is vibrated by said focused fluid columns.

It is further core purpose of the invention to provide the focused fluid columns generated by a piston actuated by a motor with an eccentric mechanism.

A further object of the invention is to disclose the method comprising a step of dispensing fixed amounts of at least one medicament by a medicament dispenser and injecting said fixed amounts of said at least one medicament into said focused fluid column.

A further object of the invention is to disclose the method comprising a step of providing a fluid by a fluid dispenser fluidly coupled to said fluid oscillator.

It is further core purpose of the invention to provide the focused fluid columns generated by a rotating disc having a missing section.

DETAILED DESCRIPTION OF PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a pulse inhaler and method of pulsed inhaling.

The term 'inhaler' refers hereinafter to an apparatus used for inhaling medicinal substances or air. The inhaler according to the present invention comprises a fluid oscillator providing a focused fluid column including a series of alternating high and low pressures zones; a medicament dispenser adapted for releasing small and fixed amounts of medicaments via the fluid column; and at least one outlet orifice adapted to direct said focused fluid column towards the respiratory tract of the patient, wherein said small and fixed amounts of medicaments are applied to the patient concomitantly vibrating gently, continuously and continually the patient's respiratory tracts.

According to one embodiment of the present invention, the pulsed fluid is a compressible gas, such as air, carbon dioxide etc. Additionally or alternatively, the fluid is in a liquid form, such as water or other water miscible solution, organic solvents, singled-phased or multi-phased fluids, homogeneous or heterogeneous diluents or any combination thereof. A mixture of liquid and gas and fine particles containing fluids are also possible.

According to one embodiment of the present invention, the inhaler additionally comprises a heating/cooling means, wherein the temperature of the fluid is conditioned to a predetermined value before being applied to the respiratory tract of the patient. Electrical heating means elevates the temperature of the inhaled fluid from its ambient temperature to preferably about 37° C. to 42° C. Humidifying means are also possible to be incorporated.

According to one embodiment of the present invention, the medicament is in a solid phase. Hence, the medicament may be selected from granular matter, a drug sized to form fine particles, powder, sol, gel, sol-gel, glass, encapsulated matter, milled composition or any combination thereof Alternatively or additionally, the medicament may be utilized in a liquid phase. In such a case, the fluid is selected in a non limiting manner from water miscible compositions, water immiscible compositions, emulsions, extracts, dispersions, suspensions, vasiculated solutions, aggregated phases or any combination thereof.

It is according to another embodiment of the present invention wherein the fluid or the medicament is selected in a non-limiting manner from at least one of the group of Braochodilators, especially sympatic mimetics, alfa antagonists, anti cholinergics; nasal decongestants, such as pseudoehedrines, ephedrines; steroids; anti histamines; anti prostaglandins, alternative or homeopathic medicaments; vaso constrictors; local anesthetics; mast cell stabilizers; antibiotics, such as biocides, fungicides etc; pleasant odor; pheromones; hormone treatments, such as ADH, insulin, growth hormones; vapors, humidifiers; drying compositions; hot or cold vapors; hyper-, iso- or hypotonic vapors or any combination thereof, or decongestants, essential oils, volatile compounds, etheric oils, terepenes, terpanols and either water miscible or water-immiscible extracts, especially oils or extracts obtained from Amyris, Balsam, Bay Rum, Black Pepper, bornyl acetate, Cajeput, Camphor, Cedarwood, Cedarleaf oil, Chamomile, chlorbutanol, Cinnamon, Clary Sage Rosewood, Clove, Eucalyptus, Frankincense, Geranium, Ginger, Lavender, Lemon, Lemon essential oils, levomenthol, Lime, Menthol, Mint, Myrrh, nutmeg oil Orange, Patchouli, Peppermint, Pine Needle, Rose Eucalyptus, rosemary, Rosewood, Sage, Sandalwood, Spearmint, Tea Tree, terpinol, turpentine oil, thymol, Ylang Ylang or any combination thereof.

Otherwise, and still in a non-limiting manner, the aforesaid medicament is at least one of the group of compositions and commercial available medicaments, their derivatives, or by-products provided thereof, selected from: Acrivastine, Aller-Eze Clemastine, Aller-Eze nasal spray, Azatadine maleate, Azelastine nasal spray, Beclometasone nasal spray, Beclometasone nasal spray, Beconase hayfever nasal spray, Beconase hayfever relief for adults, Beconase nasal spray, Benadryl allergy relief, Benadryl, Benadryl, Benadryl plus, Brompheniramine maleate, Budesonide nasal spray, Calimal Antihistamine, Cetirizine, Chlorphenamine, Clarityn, Clemastine, Cyproheptadine hydrochloride, Desloratadine, Dexa-Rhinaspray Duo. Dimotane elixir, Dimotane plus, Dimotapp elixir, Dimotapp elixir paediatric. Dimotapp LA, Flixonase allergy nasal spray, Flixonase aqueous nasal spray, Fluticasone propionate nasal spray, Galpharm hayfever and allergy relief, Galpseud Plus, Haymine, Histafen, Ipratropium bromide nasal spray, Levocabastine nasal spray, Levocetirizine dihydrochloride, Livostin direct nasal spray, Livostin nasal spray, Loratadine, Medised, Medised, Mistamine, Mizolastine, Mizollen, Mometasone furoate nasal spray, Nasacort, Nasobec nasal spray, Nasonex nasal spray, Neoclarityn tablets/syrup, Optimine syrup, Periactin, Phenergan, Piriteze, Piriton, Pollenase hayfever nasal spray, Promethazine hydrochloride elixir, Promethazine hydrochloride, Rhinocort Aqua, Rhinolast allergy nasal spray, Rhinolast nasal spray, Rinatec nasal spray, Rino clenil nasal spray, Rynacrom allergy nasal spray, Rynacrom nasal spray, Semprex, Sodium cromoglicate nasal spray, Sudafed Plus, Syntaris nasal spray, Tavegil, Telfast 120, Terfenadine, Terfinax, Triamcinolone acetonide, Vista-Methasone, Xyzal tablets, Zirtek allergy relief tablets, Zirtek allergy tablets/solution, Afrazine, Anadin, Beechams all-in-one, Beechams products, Benylin products, Contac, Day Nurse, Dimotapp elixir, Dimotapp elixir paediatric ,Dimotapp products, Galpseud, Karvol decongestant products, Lemsip products, Meggezones, Merocets Plus lozenges, Nurofen Cold and Flu, Otrivine Menthol Nasal Spray, Otrivine Metered Dose Sinusitis Spray, Otrivine prducts, Pseudoephedrine hydrochloride, Sterwin real lemon cold powders and other products, Strepsils Menthol and Eucalyptus and other products, Sudafed and its products, Xylometazoline nasal drops, Bactroban Nasal, Fusafungine, Locabiotal, Naseptin nasal cream, Ipratropium bromide nasal spray, Rinatec nasal spray, pseudoephedrine, propylhexedrine, L-Desoxyephedrine, xylometazoline hydrochloride or any combination thereof. Inhaling of a dispersed medicament while vibrating the respiratory tract is thus the core of the present invention.

It is according to another embodiment of the present invention, the medicament is activated before or while being carried by the fluid column. The activation is provided by physical, chemical and/or biological means. Hence, for example, at least one ingredient of the medicament of at least a portion of the medicament is heated, radiated, emitted by UV, sonicated, vibrated etc; oxidized, polymerized, trans-esterified, hydrolyzed or subjected to enzymological reactions.

It is according to another embodiment of the present invention, the medicament is introduced to the dispenser by means of a disposable capsule or the like. The capsule comprises an envelope adapted to be punctured such that at least a limited amount of the medicament contained in the capsule is forced to flow towards the pulsed column of fluid in a predetermined flux.

It is according to another embodiment of the present invention, the fluid oscillator is at least one moving piston. Preferably, the piston is actuated by means of a motor connected to an actuator. In this mechanism, an electrically or mechanically rotating motor periodically actuates a shaft connected to the actuator and the piston. The piston compresses the fluid inside a pressure chamber and segments the air column into segments. The fluid is released from the pressure chamber in predetermined intervals via at least one outlet orifice, adapted to direct and focus the fluid column towards the respiratory tract of the patient. It is acknowledged in this respect that the fluid column is generated as oscillating fluid comprising a series of alternating low and high pressure peaks. This pulsed fluid column is especially adapted to vibrate the respiratory tract of the patient thereby causing smooth muscle relaxation, reduction of airway edema, increases in the blood and the lymphatic flows, improved gas exchange and oxygenation and decreased dyspnea.

The high pressure peaks of the fluid column transport the medicament to the patient's airways. Since the medicament is transported in the high pressure peaks, the delivery of the drug does not rely on the patient's ability to inhale the drug into his lungs, resulting in a decrease in drug deposits in the oral cavity and side effects of taking the drug.

While the pulsed fluid column gently, continuously and continually vibrates the respiratory tract of the patient, small portions of the medicaments are transported through wider, more relaxed and less edematous airways, penetrating further into the lungs and to the medium and small sized airways, increasing efficacy and reducing the side effects to the patient.

The vibrations improve mucociliary clearance of secretions in lungs and airways, thus preventing accumulation of secretions and diseases.

Furthermore, the pulsation, when applied during expiration, can help to prevent airway collapse during an asthma or COPD attack.

Reference is made now to FIG. 1, schematically presenting a lateral section of the inhaler according to one simple embodiment of the present invention. The inhaler 100 comprises a piston (103) actuated by a motor and an actuator (105). Air 101 enters the inhaler 100 through an adjustable inlet valve (102) and flows through a heating chamber (107), which optionally heats the air flow and is activated by an air conditioning switch (111). The movement of the piston 103 generates pulses of compressed air 109, which exits the inhaler 100 via outlet orifice 108. An On/Off switch (104) operates the inhaler 100. One battery or more (106) supplies the electrical power. A plurality of rechargeable 1.5V batteries are presented in item number 106. An optional sensor 110 is also illustrated, adapted to determine the direction of air flow through the inhaler 100, either inhaled air and/or exhaled air.

Reference is made now to FIGS. 2A and 2B, schematically presenting a lateral projection (upper view) of a pulsed inhaler 200 according to another embodiment of the present invention. This medical device 200 comprises a fluid oscillator, including, inter alia, a turbine (201) and a piston (203), which is coupled to an actuator and motor 202, an on/off switch (204), an air inlet (205), a dispensing module (206) adapted to dispense disposable compositions and/or air, a fluid container (207), a fluid-medicament switching means (208), a capsule housing (209), a warmed air stream (220) conditioned to about 37° C., a heating chamber 210, a dispensing rim (211) located adjacent to the respiratory tract of the patient, and a dispensing orifice (212) also denoted as a fluid outlet, a flow direction sensor (213), an air conditioning switch (214), and an AC supply means (215).

Reference is made to FIG. 2B, which presents an inhaler configuration 250 of similar construction to the inhaler 200 shown in FIG. 2A, in which the fluid container 207 is omitted, and the medicament is mixed with compressed air 252.

It is also within the scope of the invention, that the fluid oscillator includes a rotating disc of any shape or size. The disc having a missing portion thereof is especially preferred. Small portions of medicaments are dispersed towards the rotating disc, while a turbine continuously and continually forces fluid (normally air) via a Bernoulli pipe, e.g., a conic pathway wherein the wide inlet draws-in air which is forcefully streamed via a narrower outlet, such that fixed amounts of the medicament are ejected through the outlet orifice to the patient. The rotating disc and the turbine may share a single motor.

Figure 3:
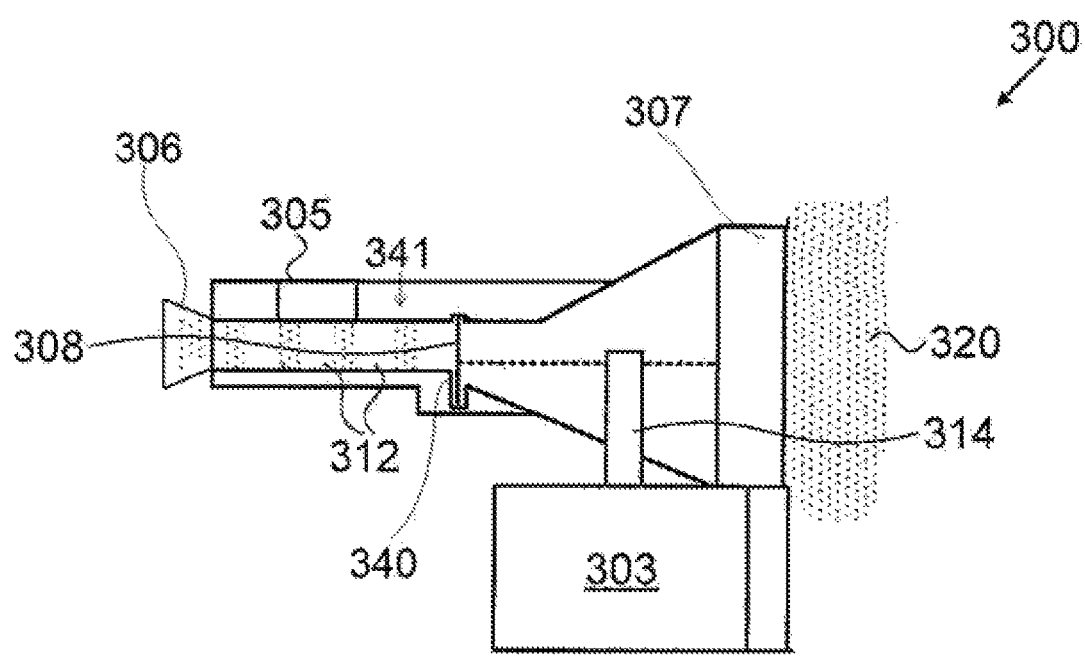
FIG. 3 schematically presents a lateral section of a rotating disc inhaler according to an embodiment of the present invention.

Reference is now made to FIG. 3, presenting a cross-sectional view of a disc-containing pulse inhaler. The aforesaid inhaler comprises a rotating disc 308 having a missing section. External air 320 is supplied to the inhaler 300 at an inlet to the turbine 307 driven by an electric motor 303. The rotating disc 308 is cooperatively disposed within a notch 340 of an air passage 341 such that the rotating disc 308 by turns allows and blocks an air flow from the air turbine 307 to an outlet orifice 306. Thus, an air flow characterized by a train of pneumatic pulses is generated.

Figure 4A:
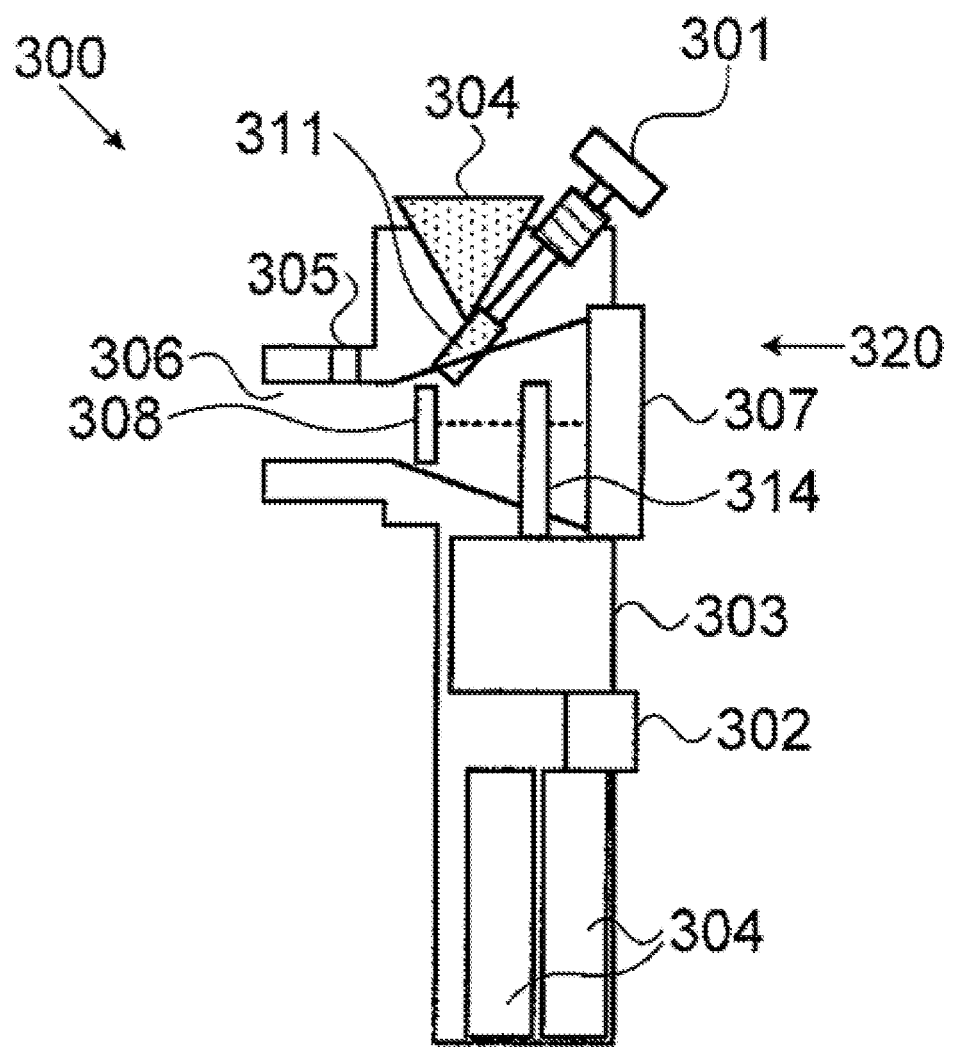
FIGS. 4A, 4B and 4C schematically present a lateral cross section of a disc pulsed inhaler according to yet another embodiment of the present invention.
Figure 4B:
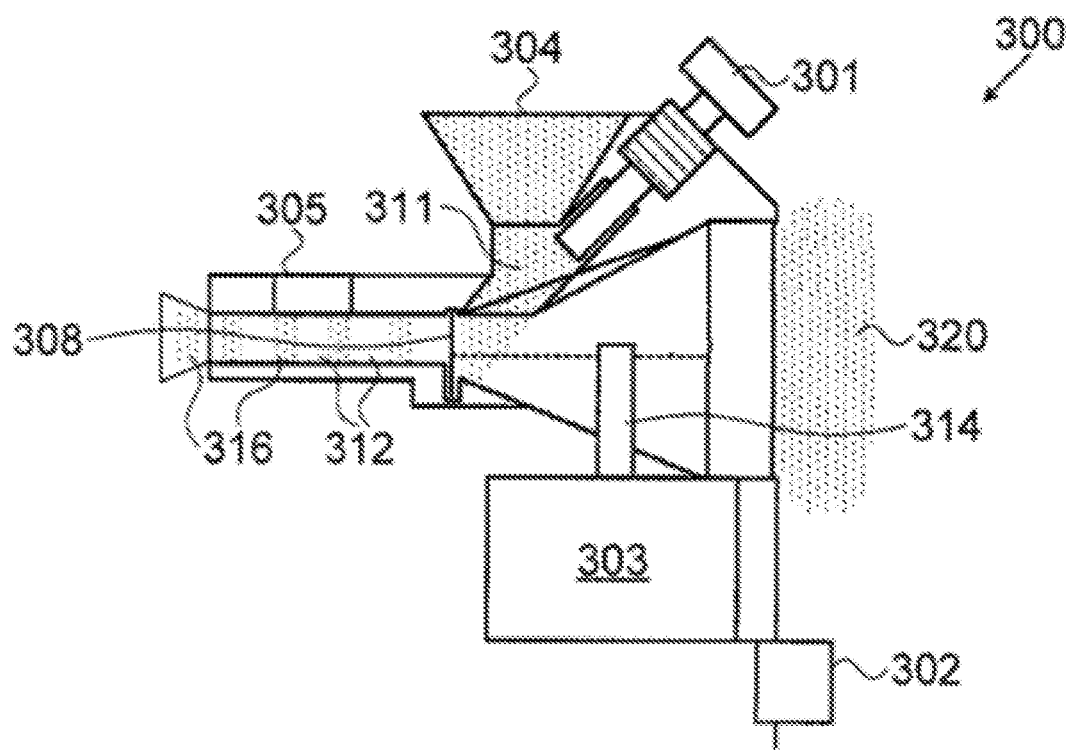

Reference is made now to FIGS. 4A and 4B, which present a lateral section of a disc-containing pulse inhaler 300 according to yet another embodiment of the present invention. A medicament dispensing pusher (301) dispenses a small amount of medicament 311 from a medicament container (304). Concomitantly with dispensing the medicament 311, both an air turbine (307) and at least one rounded disc (308), with a missing portion 310, are rotated such that pulsed fluid column 312 is ejected via an outlet orifice (306). External air 320 is supplied to the inhaler 300 at an inlet to the turbine 307. In this device 300, a motor (303) actuates both the turbine (307) and the disc (308). An on/off switch (302) may regulate and/or activate the motor 303. A top view of the disc (308) is also presented (FIG. 3D). It is acknowledged in this respect that the amount of the dispensed medicament 311 is also regulated by the size and shape of the rotating disc (308) and the missing portion 310 thereof. Optionally, a sensor (305) may be also provided. The pusher 301 may also include a dosage indication window 314 for indicating to the patient the termination of the medicament in the inhaler 300.

FIG. 3B schematically illustrates the disc-containing inhaler 300 in a lateral section, showing the pulsed fluid column 312 and the small amounts of the medicaments 316 transported by the pulsed fluid column 312.

It is also within the scope of the present invention that the disc-containing inhaler 300 as shown in FIGS. 4A and 4B is comprised of a fluid turbine (307); a medicament dispenser (304) adapted for releasing small and fixed amounts of at least one the medicament 311 via the pulsed fluid column 312; a fluid and medicament oscillator 300 providing a focused fluid column 312 including a series of alternating high and low medicaments concentrations; the oscillator includes one or more rotating discs 308, especially discs comprising missing portions 310 thereof; and, at least one outlet orifice (306) directing said focused fluid column 312 towards the respiratory tract of the patient, wherein said small and fixed amounts of medicament 311 are subjected to the patient concomitantly the patient's respiratory tract is gently, continuously and continually vibrated by the focused air column.

Figure 4C:
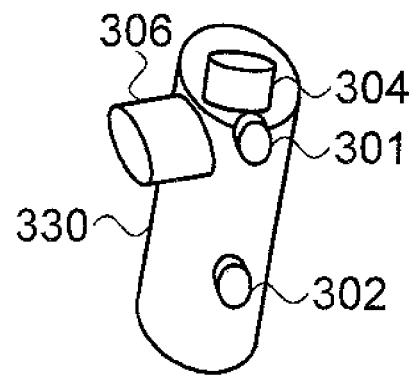
Figure 4D:
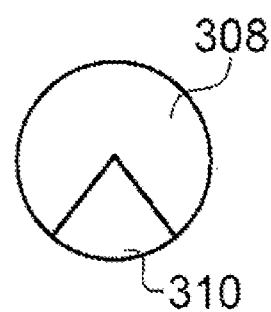
FIG. 4D shows a rotating disc with a missing portion, in accordance with yet another preferred embodiment of the present invention, and FIGS. 5A and 5B schematically present a lateral cross-section of a disc-inhaler according to a further embodiment of the present invention, comprising at least one valve adapted to facilitate medicament dispensing during inhalation (FIG. 5B) and exhalation (FIG. 5A).

Reference is made now to FIG. 4C, which presents a general view of the dispensing portion 330 of the inhaler 300, including, inter alia, the medicament dispensing pusher 301, the medicament dispenser 304, the on/off switch 302 and the outlet orifice 306.

According to a further embodiment of the present invention the medicament is contained in a capsule. The insertion of this capsule initiates the medicament delivery by means of a micro-switch triggered by the pressure of the capsule on the micro-switch when the dispensing chamber is closed. The capsule provides coded information for activating the dispensing of the medicament. It is another embodiment of the present invention in which the medicament delivery is provided by a 2D (2-dimensional) verification device, such as a bar-code or a 3D (3-dimensional) specific and predetermined fitting mechanism, e.g., fitting by means of shape and size. In a further embodiment of the present invention the shape of the capsules inside the inhaler envelope provides lock-in-key information for activating the inhaler It is further within the scope of the present invention, that the medicament is forced towards the client respiratory tract directly as defined above or indirectly, e.g. via one or more dispensing means being either active or passive. Active dispensing means are selected in a non-limiting manner from medicament dispensers, such as inhalers of Ventolin™ (salbutamol™) or the like, humidifiers etc. It is thus according to one embodiment of the present invention wherein the dispersed medicaments forced outside the invented device is fed into said active dispensers. Passive dispensing means are either flexible or rigid pipes, tubes and other conducting means adapted to force or purge at least a portion of the dispersed material towards a predetermined, e.g., focused target being either adjacent to the invented device or located in a remote location.

Figure 5A:
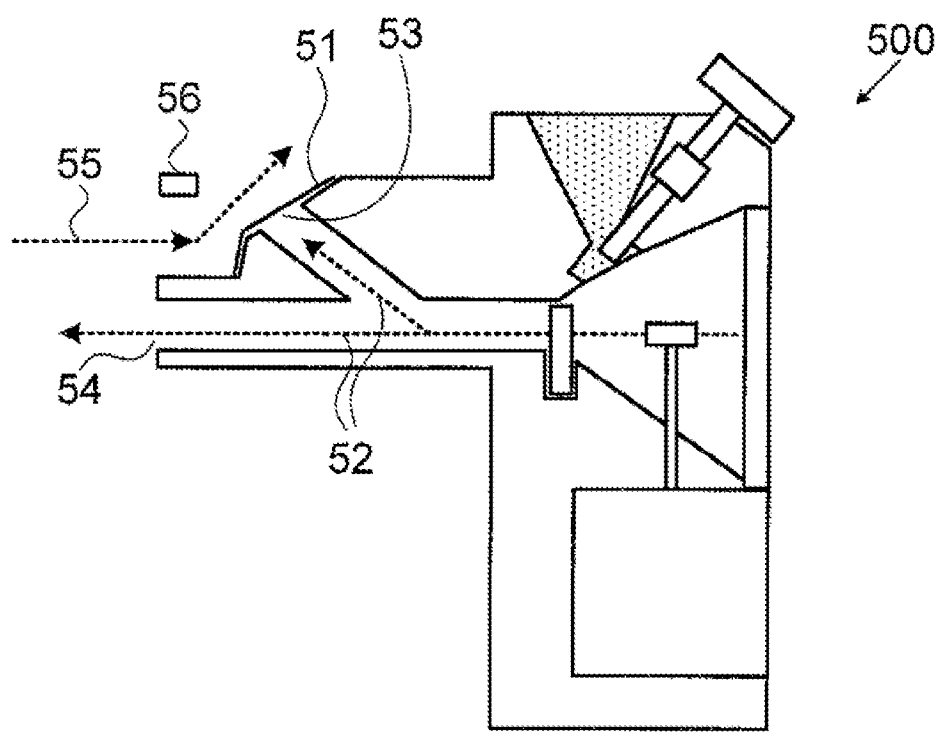
Figure 5B:
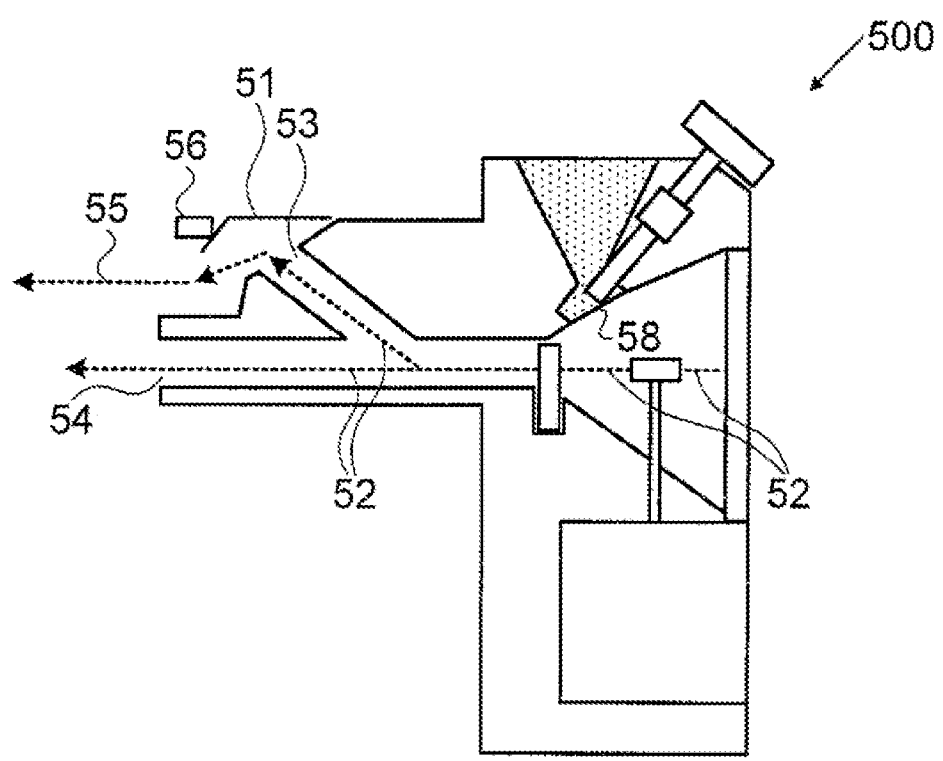

Reference is also made now to FIGS. 5A and 5B, which present a valve-containing pulsed inhaler, such as a disc-inhaler 500. A unidirectional valve or valves are adapted to separate between the inhalation and exhalation steps of the respiratory tract. FIG. 5A illustrates a cross-section of the inhaler in its closed-valve configuration during exhalation, wherein a valve (51) is positioned such that external air 55 cannot enter the inhaler 500 through an inhalation aperture (53) and a dispensed medicament air column (52) is exhausted through both the exhalation aperture (54). FIG. 5B illustrates, however, a cross-section of the valve-containing pulsed inhaler 500 in an open-valve configuration during inhalation, wherein valve (51) abuts an abutment 56 in such a manner that external air is directed to enter the inhaler 500 via the inhalation aperture (53), while dispensing a medicament 58 into a pulsed air column 52 and exhausted solely via exhalation aperture (54).

The invention claimed is:

1. A pulsating inhaler comprising:
   a. a fluid straight hollow passage defined by an internal surface thereof; said fluid straight hollow passage having an inlet and an outlet thereof;
   b. a blower coupled to said inlet of said fluid straight hollow passage; said blower generating a fluid flow conducted by said fluid straight hollow passage from said inlet to said outlet;
   c. a rotating disc having a missing section and mounted within said fluid straight hollow passage between said inlet and said outlet thereof; said rotating disc disposed within a notch made in said internal surface of said fluid straight hollow passage; said rotating disc providing focused fluid columns with a series of alternating high and low pressure zones; and d. at least one outlet orifice fluidly connected to said outlet and spaced longitudinally from said notch; said at least one outlet orifice adapted for delivering said focused fluid column to a respiratory tract of said patient;

said pulsating inhaler further comprises a medicament dispenser configured for dispensing at least one medicament from a top portion of a housing of the pulsating inhaler into said fluid flow within said fluid straight hollow passage upstream and adjacent to said rotating disc.

2. The inhaler according to claim 1, wherein said medicament dispenser is activated before fixed amounts of said at least one medicament is transported by said focused fluid column.

3. The inhaler according to claim 2, wherein said at least one medicament is dispensed by puncturing a disposable capsule such that a fixed amount of said medicament is dispensed into said focused fluid column.

4. A method of administering focused fluid columns to the respiratory tract of a patient, said method comprising the steps of:

a. providing a pulsating inhaler further comprising:

i. a fluid straight hollow passage defined by an internal surface thereof; said fluid straight hollow passage having an inlet and an outlet thereof;

ii. a blower coupled to said inlet of said fluid straight hollow passage; said blower generating a fluid flow conducted by said fluid straight hollow passage from said inlet to said outlet;

iii. a rotating disc having a missing part and mounted within said fluid straight hollow passage between said inlet and said outlet thereof; said rotating disc disposed within a notch made in said internal surface of said fluid straight hollow passage; said rotating disc providing focused fluid columns with a series of alternating high and low pressure zones;

iv. at least one outlet orifice fluidly connected to said outlet and spaced longitudinally from said notch; said at least one outlet orifice adapted for delivering said focused fluid column to the respiratory tract of said patient; and v. a medicament dispenser configured for dispensing at least one medicament from a top portion of a housing of the pulsating inhaler into said fluid flow generated by said blower upstream and adjacent to said rotating disc;

b. generating said fluid flow generated by said blower;

c. conducting said fluid flow within said fluid straight hollow passage;

d. dispensing said at least one medicament into said fluid flow upstream relative to said rotating disc;

e. providing said focused fluid columns by said rotating disc;

f. inhaling said focused fluid columns such that a respiratory tract of said patient is vibrated by said focused fluid columns.

5. The method according to claim 4 further comprising a step of providing a fluid by a fluid dispenser fluidly coupled to said rotating disc.

* * * * *